(12) United States Patent
Tanaka et al.

(10) Patent No.: US 12,018,319 B2
(45) Date of Patent: Jun. 25, 2024

(54) METHOD AND DEVICE FOR DIGITAL PCR MEASUREMENT

(71) Applicant: HITACHI, LTD., Tokyo (JP)

(72) Inventors: Junko Tanaka, Tokyo (JP); Tatsuo Nakagawa, Tokyo (JP); Yuzuru Shimazaki, Tokyo (JP); Kunio Harada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 792 days.

(21) Appl. No.: 16/973,990

(22) PCT Filed: May 20, 2019

(86) PCT No.: PCT/JP2019/019946
§ 371 (c)(1),
(2) Date: Dec. 10, 2020

(87) PCT Pub. No.: WO2019/239805
PCT Pub. Date: Dec. 19, 2019

(65) Prior Publication Data
US 2021/0130877 A1 May 6, 2021

(30) Foreign Application Priority Data
Jun. 14, 2018 (JP) ................. 2018-113894

(51) Int. Cl.
*C12P 19/34* (2006.01)
*B01L 3/00* (2006.01)
*C12Q 1/6825* (2018.01)

(52) U.S. Cl.
CPC .......... *C12Q 1/6825* (2013.01); *B01L 3/5027* (2013.01); *B01L 2200/147* (2013.01); *B01L 2300/0816* (2013.01); *B01L 2300/0883* (2013.01); *B01L 2400/0415* (2013.01); *B01L 2400/0487* (2013.01); *C12Q 2531/113* (2013.01); *C12Q 2563/107* (2013.01)

(58) Field of Classification Search
CPC .................................................. C12Q 1/6851
See application file for complete search history.

(56) References Cited

U.S. PATENT DOCUMENTS

| 4,683,195 A | 7/1987 | Mullis et al. |
| 4,683,202 A | 7/1987 | Mullis |
| 4,800,159 A | 1/1989 | Mullis et al. |
| 5,780,233 A | 7/1998 | Guo et al. |
| 2011/0002845 A1 | 1/2011 | Cheng |
| 2011/0207622 A1 | 8/2011 | Wong et al. |
| 2011/0244455 A1 | 10/2011 | Larson et al. |
| 2012/0010821 A1 | 1/2012 | Hirano et al. |
| 2019/0330679 A1* | 10/2019 | Kim ..................... C12Q 1/6853 |
| 2021/0241857 A1* | 8/2021 | Fraley .................... G16B 30/00 |
| 2023/0068047 A1* | 3/2023 | Bernier ................ C12Q 1/6851 |

FOREIGN PATENT DOCUMENTS

| JP | 2000-511434 A | 9/2000 |
| JP | 2010-529954 A | 9/2010 |
| JP | 2012-029689 A | 2/2012 |
| JP | 2013-521763 A | 6/2013 |
| JP | 2013-521764 A | 6/2013 |
| WO | 2018-128013 A1 | 7/2018 |

OTHER PUBLICATIONS

Sinha M. et al., A High-Resolution Digital DNA Melting Platform for Robust Sequence Profiling and Enhanced Genotype Discrimination, SLAS Technology, Apr. 13, 2018, vol. 23, No. 6, p. 580-591, Abstract, Figure 4 etc.
Fraley S. I. et al., Universal digital high-resolution melt: a novel approach to broad-based profiling of heterogeneous biological samples, Nucleic Acids Research, vol. 41, No. 18, 2013, e175, Abstract, Figure 1, etc.
Tanaka J. et al., KRAS genotyping by digital PCR combined with melting curve analysis, Scientific Reports, vol. 9, 2626, Feb. 2019, Abstract, Figure 1, etc.
Genome Res., vol. 10, pp. 986-994, 1996.

* cited by examiner

*Primary Examiner* — Kenneth R Horlick
(74) *Attorney, Agent, or Firm* — Volpe Koenig (57) ABSTRACT

The present invention addresses the problem of providing a novel digital PCR analysis method. One embodiment of the novel digital PCR analysis method is a DNA detection method including the steps of: partitioning a DNA solution containing a fluorescent-labeled probe or a DNA intercalator and a target DNA to be detected into a plurality of compartments; carrying out a nucleic acid amplification reaction in the compartments; measuring a fluorescence intensity in association with a temperature change; calculating a melting temperature of a DNA double strand based on a change in the fluorescence intensity in association with the temperature change; and calculating a ratio of a fluorescence intensity at a second temperature that is lower than a first temperature in association with the temperature change to that at the first temperature.

15 Claims, 9 Drawing Sheets

Specification includes a Sequence Listing.

| GENE | TYPE OF MUTATION | NUMBER OF SAMPLE SOLUTIONS |
|---|---|---|
| ONCOGENE A | WILD-TYPE | 2000 |
| ONCOGENE A | MUTANT a | 20 |
| ONCOGENE A | MUTANT b | 100 |
| EMPTY | | $5 \times 10^6$ |

FIG. 10

| GENE | TYPE OF MUTATION | PERCENTAGE (%) |
|---|---|---|
| ONCOGENE A | WILD-TYPE | 94 |
| ONCOGENE A | MUTANT a | 0.1 |
| ONCOGENE A | MUTANT b | 5 |
| ONCOGENE B | WILD-TYPE | 80 |
| ONCOGENE B | MUTANT c | 10 |
| ONCOGENE B | MUTANT d | 10 |

METHOD AND DEVICE FOR DIGITAL PCR MEASUREMENT

CROSS-REFERENCE TO RELATED APPLICATION

This application claims priority from prior Japanese Patent Application No. 2018-113894, filed on Jun. 14, 2018, the entire contents of which are incorporated herein by reference.

TECHNICAL FIELD

The present invention relates to methods and devices both for a digital PCR measurement.

BACKGROUND ART

Digital PCR (Japanese Translation of PCT International Application Publication No. 2013-521764) has been developed as a method for solving the problem that measurement reproducibility is decreased when the amount of a target gene is trace in the conventional genetic tests such as PCR (U.S. Pat. Nos. 4,683,195, 4,683,202 and 4,800,159) and real-time PCR (Genome Res., vol. 10, pp. 986-994, 1996). When digital PCR is employed, a trace amount of DNA can be quantified using a limiting-diluted sample, in which the result of the detection of the DNA is determined as "0 (absent)" or "1 (present)".

Hereinbelow, one example of the digital PCR detection method will be described. Firstly, a DNA polymerase, a primer and a fluorescent-labeled probe, which are necessary for PCR, are added to a limiting-diluted sample, and droplets of the PCR reaction solution are generated in an oil. Each of the droplets thus generated contains one molecule of a target gene or does not contain the target gene. Subsequently, the target gene in each of the droplets is amplified by PCR. After the PCR, the fluorescence intensity of each of the droplets is measured, and then the number of droplets each having a fluorescence intensity larger than a threshold value is counted. In this manner, the target gene can be quantified. In the digital PCR of this type, a limiting-diluted sample is used. Therefore, influence of a sample-derived component that may become an inhibiting factor for PCR can be eliminated. Furthermore, the digital PCR does not need the use of a calibration curve, and therefore an absolute amount can be measured directly.

SUMMARY OF INVENTION

Technical Problem

In the common PCR, it is known that the reaction efficiency is decreased for the reason that a reaction-inhibiting substance is present in a reaction solution, a secondary structure of a template DNA is formed, the designing of primers is unsatisfactory or the like. In digital PCR, in contrast, DNA is measured at the end-point. Therefore, it has been believed that the reaction efficiency of the PCR does not have much influence on the results of the measurement. However, actually, even when the DNA is measured at the end-point in digital PCR, the fluctuations in fluorescence intensities become large due to the non-equality of the PCR reaction efficiency in the individual droplets, resulting in the decrease in measurement reproducibility and measurement accuracy of the digital PCR.

Under these circumstances, for the purpose of improving the measurement reproducibility and measurement accuracy of digital PCR, the present inventors have developed a technique for enabling the identification of a target gene in each of droplets by measuring the melting temperature (Tm) of a PCR amplicon even if the PCR reaction efficiencies in the droplets are unequal. More specifically, for example, droplets that have undergone PCR are arranged planarly and then the melting temperature (Tm) of the target gene amplified in the droplets and a fluorescent-labeled probe is measured. As a result, it becomes possible to identify the genotype of the target gene based on the difference in melting temperatures even if the PCR reaction efficiencies in the droplets are unequal.

On the other hand, in digital PCR, 90% of droplets are empty droplets that do not contain the target gene. Therefore, for improving measurement reproducibility and measurement accuracy, it is critical to distinguish empty droplets that do not contain the target gene using a measurement device and to remove the empty droplets from the data to be analyzed. However, in empty droplets that do not contain the target gene, a substance with which a fluorescent-labeled probe can hybridize does not present. Therefore, the empty droplets cannot be specified based on a melting temperature. Meanwhile, it has been found that the identification of empty droplets that do not contain a target gene, based on fluorescence intensity as in the case of the conventional digital PCR, is difficult for the following reasons. First of all, a molecular beacon, which is a fluorescent-labeled probe that has been used for a melting curve analysis, does not have a structure that can be sensitized through the decomposition thereof during PCR, unlike TaqMan (registered trademark) probe that has been used in the conventional digital PCR. Therefore, when the molecular beacon is used, even in positive droplets that contain a target gene, the fluorescence intensity after PCR is weak. Second, since the fluorescence intensity is measured with the droplets widely spread planarly, in-plane fluctuations in the fluorescence intensity occur upon the irradiation with light and the capture of fluorescence. For these reasons, the fluorescence intensity in the droplets in which a target gene is amplified becomes weak, and the overall fluctuations in fluorescence intensity in the droplets become large. As a result, a signal (S)/noise (N) ratio may become small, leading to the decrease in accuracy of the distinction between an empty droplet that does not contain a target gene and a droplet that contains the target gene based on fluorescence intensities.

The object of the present invention is to provide novel measurement methods and novel measurement devices for digital PCR, which make it possible to distinguish empty droplets that do not contain a target gene with the measurement device and to remove the empty droplets from data to be analyzed in digital PCR employing a melting curve analysis.

Solution to Problem

The present inventors have found that empty droplets that do not contain a target gene show a small change in fluorescence intensity in association with an increase in temperature while droplets that contain the target gene show a large change in fluorescence intensity in association with the increase in temperature in digital PCR employing a melting curve analysis; therefore, the empty droplets that do not contain the target gene can be distinguished with high accuracy by measuring the ratio of the fluorescence intensity at a lower temperature to that at a higher temperature. This finding leads to the accomplishment of the present invention.

One aspect of the present invention is a DNA detection method including the steps of: partitioning a DNA solution containing a fluorescent-labeled probe or a DNA intercalator and a target DNA to be detected into a plurality of compartments; carrying out a nucleic acid amplification reaction in the compartments; measuring a fluorescence intensity in association with a temperature change; calculating, in association with the temperature change, a melting temperature of a DNA double strand based on a change in the fluorescence intensity; and calculating, in association with the temperature change, a ratio of a fluorescence intensity at a second temperature to a fluorescence intensity at a first temperature, the second temperature being lower than the first temperature. The DNA detection method may further include the step of identifying a compartment for which the calculated ratio of the fluorescence intensity is equal to or less than a predetermined threshold value as a compartment that does not contain the target DNA. The DNA detection method may further include the step of identifying a compartment for which the calculated ratio of the fluorescence intensity falls within a predetermined range as a compartment that contains the target DNA.

In any one of the above-mentioned DNA detection methods, it is possible that the DNA solution contains a fluorescent-labeled probe and the melting temperature is a melting temperature of a double strand formed between the fluorescent-labeled probe and the target DNA. In this regard, the fluorescent-labeled probe may have a fluorescent dye and a quencher for the fluorescent dye. Alternatively, it is also possible that the DNA solution contains a DNA intercalator and the melting temperature is a melting temperature of a double strand of the target DNA.

In any one of the above-mentioned DNA detection methods, the plurality of compartments may be arranged planarly. Furthermore, the DNA solution may be partitioned into the plurality of compartments in a form of droplets or by using wells.

Another aspect of the present invention is a DNA detection device for detecting a target DNA to be detected in a DNA solution, including: a heater for heating the DNA solution; a fluorescence measurement unit for measuring a fluorescence intensity emitted from the DNA solution; and a calculator for calculating, in association with a temperature change of the DNA solution, a melting temperature of a DNA double strand based on a change in a fluorescence intensity and then calculating a ratio of a fluorescence intensity at a second temperature to a fluorescence intensity at a first temperature, the second temperature being lower than the first temperature. The DNA detection device may further include an amplification unit for amplifying the target DNA. The DNA detection device may further include a monitor on which the result of the detection is displayed.

Still another aspect of the present invention is a program for allowing a DNA detection device such as any one of the above-mentioned DNA detection devices to execute any one of the above-mentioned DNA detection methods.

Further aspect of the present invention is a non-statutory recording medium for storing the above-mentioned program.

DESCRIPTION OF EMBODIMENTS

The objects, features and advantages of the present invention and ideas thereof will be obvious to those skilled in the art from the statements set forth in the description, and the present invention can be reproduced easily by those skilled in the art based on the statements set forth in the description. It is understood that the embodiments, specific examples and the like described hereinbelow illustrate preferred embodiments of the present invention and are for illustrative purpose only, and that the present invention is not to be limited by these embodiments and examples. It will be obvious to those skilled in the art that various changes and modifications can be made based on the statements set forth in the description within the spirit and scope of the present invention disclosed herein.

(1) Principle and Effects of DNA Detection Method

The DNA detection method according to the present invention includes the steps of: partitioning a DNA solution containing a fluorescent-labeled probe or a DNA intercalator and a target DNA to be detected into a plurality of compartments; carrying out a nucleic acid amplification reaction in the compartments; measuring a fluorescence intensity in association with a temperature change; and calculating, in association with the temperature change, a melting temperature of a DNA double strand based on a change in the fluorescence intensity.

Figure 1:
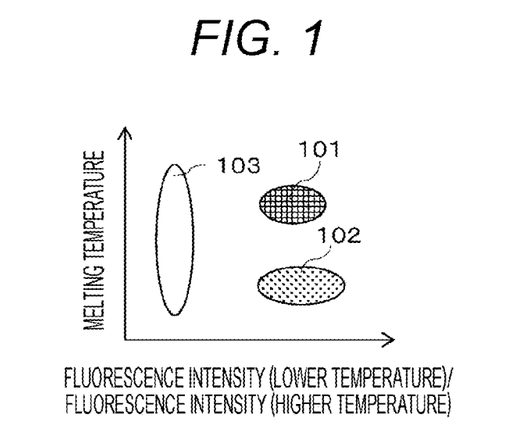
FIG. 1 is a diagram showing the basic concept of a DNA detection method according to one embodiment of the present invention, which is carried out using the ratio, in association with a temperature change, of the fluorescence intensity of a PCR amplicon at a second temperature to that at a first temperature, the second temperature being lower than the first temperature, in digital PCR employing a melting curve analysis.
Figure 2:
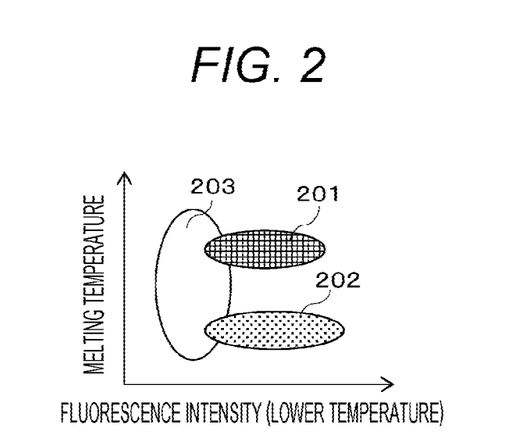
FIG. 2 is a diagram showing the basic concept of a DNA detection method according to one embodiment of the present invention, which is carried out using a melting temperature (Tm) of a PCR amplicon in digital PCR employing a melting curve analysis.

FIG. 1 shows an example of the measurement result which is envisaged in a typical embodiment of the DNA detection method and is obtained by calculating, in association with the temperature change, the ratio of the fluorescence intensity at a second temperature that is lower than a first temperature to that at the first temperature. FIG. 2 shows an example of the measurement result of digital PCR employing a melting curve analysis, wherein the DNA detection is carried out using a melting temperature (Tm) of a PCR amplicon.

In the digital PCR employing a melting curve analysis, the determination of the genotype is carried out using the fact that the melting temperature between a fluorescent-labeled probe and DNA varies depending on the genotype. The example shown in FIG. 2 is a diagram that schematically shows the measurement result of the melting temperature of DNA in droplets using fluorescent-labeled probes each corresponding to the wild-type of a target gene and a mutant of the target gene. In this regard, as the fluorescent-labeled probes, molecular beacons can be used for example. Hereinbelow, as one example, the DNA detection method using a molecular beacon will be described in detail. A molecular beacon is an oligonucleotide which is complementary to a sequence located between primers in a pair which are used in PCR for amplifying a target gene to be detected, has sequences at its both terminals which are complementary to each other, and also has a fluorescent dye and a quenching dye (quencher) at each terminal thereof. When the molecular beacon is hybridized to the target gene to be detected, the fluorescent dye and the quenching dye at each terminal of the molecular beacon are separated from each other to emit fluorescence. When the molecular beacon is dissociated from the target gene with increase in temperature, the sequences at its both terminals which are complementary to each other are hybridized with each other, and the molecular beacon forms a stem-loop structure. As a result, the fluorescent dye and the quenching dye come close to each other and the fluorescence from the fluorescent dye is quenched. In droplets 201 which contain a wild-type allele of the target gene, a fluorescent-labeled probe corresponding to the wild-type allele of the target gene is hybridized to DNA amplified by PCR to emit fluorescence, and a melting temperature corresponding to the fluorescent-labeled probe for the wild-type allele is detected. In droplets 202 which contain a mutant allele of the target gene, a fluorescent-labeled probe corresponding to the mutant allele of the target gene is hybridized to DNA amplified by PCR to emit fluorescence, and a melting temperature corresponding to the fluorescent-labeled probe for the mutant allele is detected. In empty droplets 203 which do not contain the target gene, fluorescence is not detected. In this manner, the presence or absence of the target gene having the wild-type allele and the presence or absence of the target gene having the mutant allele can be determined depending on the presence or absence of fluorescence or the types of fluorescence.

However, since the reaction efficiencies of PCR in droplets are not equal from droplet to droplet and the measurement fluctuation in the fluorescence measurement is large, the intensity of fluorescence emitted from a droplet 201 or 202 that contains the target gene cannot be different from that emitted from an empty droplet 203 that does not contain the target gene. Then, highly accurate gene detection becomes possible by measuring, in association with a temperature change, the change in fluorescence intensity of DNA in the droplets, analyzing the melting curves, and comparing the melting temperatures (Tm) with each other. For example, in empty droplets 203 that do not contain the target gene, the fluorescence intensity does not vary in association with the temperature change. Therefore, melting temperatures are not constant, and an inconstant value is obtained. On the other hand, when fluorescent dyes capable of emitting different types of fluorescence having different wavelengths are used for the fluorescent-labeled probe corresponding to the wild-type allele and the fluorescent-labeled probe corresponding to the mutant allele, it can be determined which gene is present, a gene having the wild-type allele or a gene having the mutant allele, depending on the color of the fluorescence detected. Alternatively, even when the same fluorescent dye is used for both of the fluorescent-labeled probes, it also becomes possible to determine which allele has been amplified, the wild-type allele or the mutant allele, by setting the sequences for the fluorescent-labeled probes such that the melting temperature (Tm) between one of the fluorescent-labeled probes and the target gene becomes different from the melting temperature (Tm) between the other and the target gene, carrying out a melting curve analysis and then calculating the Tm values.

As mentioned above, in digital PCR, it is possible to set a threshold value for the fluorescence intensity or a threshold value for the melting temperature by an experimenter and eliminate empty droplets which do not contain the target gene from data or count the number of droplets for each of the mutation types. However, the fluorescence in the droplets 201 which contain the wild-type allele of the target gene and the droplets 202 which do not contain the mutant allele of the target gene vary in intensity and the distributions of the fluorescence intensities are broad, while the fluorescence emitted from the empty droplets 203 which do not contain the target gene is weak and, as a result, the calculated melting temperatures can be largely variable. In this case, as shown in FIG. 2, the distributions of the droplets 201 and 202 which contain the target gene on the graph overlap with the distribution of the empty droplets 203 which do not contain the target gene on the graph, and it becomes impossible to determine the presence or absence of the gene in the overlapped regions, resulting in decrease in measurement accuracy. Particularly in digital PCR, since droplets are generated by the limiting dilution of a sample in such a manner that one or zero molecule of the target gene can be contained in a single droplet, 50 to 90% of the generated droplets are empty droplets 203 which do not contain the target gene. If the distribution of the empty droplets and the distributions of the droplets 201 and 202 which contain the target gene are overlapping with each other, quantification cannot be highly accurate.

Then, fluorescence intensity upon the hybridization of the fluorescent-labeled probe with DNA is measured both at a lower temperature and a higher temperature and the ratio between the measured fluorescence intensities is calculated. As shown in FIG. 1, the measurement results can be plotted with the x-axis as the ratios between the fluorescence intensity at the lower temperature and the fluorescence intensity at the higher temperature and with the y-axis as the melting temperatures between the fluorescent-labeled probe and the DNA. As a result, it is possible to separate the empty droplets 101 which do not contain the target gene to be detected, the droplets 102 which contain the wild-type allele of the target gene and the droplets 103 which contain the mutant allele of the target gene from one another. As a result, empty droplets which do not contain the target gene and droplets in which PCR reaction efficiency is insufficient can be distinguished reliably, resulting in the improvement in measurement reproducibility and measurement accuracy.

(2) Main Structural Elements of DNA Detection Device

The DNA detection device according to the present invention is a DNA detection device for detecting target DNA to be detected in a DNA solution, including: a heater for heating the DNA solution; a fluorescence measurement unit for measuring an intensity of fluorescence emitted from the DNA solution; and a calculator for calculating a melting temperature melting temperature of a DNA double strand from a change in the fluorescence intensity in association with a temperature change of the DNA solution, and then calculating the ratio of the fluorescence intensity of the DNA solution at a second temperature that is lower than a first temperature to that at the first temperature.

The DNA solution may be placed in any support, and may be in the form of droplets in an oil or may be in wells of a plate or the like. As an example of the DNA detection device, a DNA detection device is shown in FIG. 3A to FIG. 3D, which is equipped with a fluorescence measurement unit for measuring the color and the fluorescence intensity of a fluorescent dye contained in the DNA solution in the droplets or the wells, but the DNA detection device of the present invention is not limited thereto.

Figure 3A:
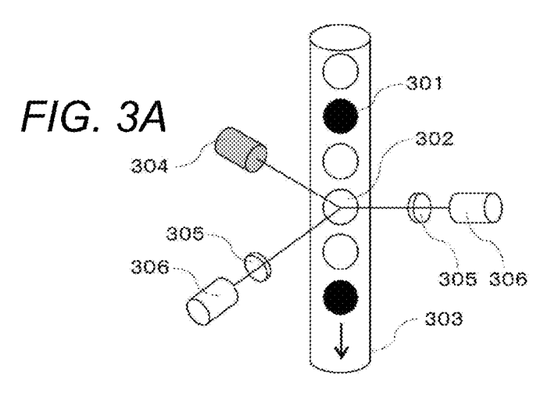
FIG. 3A to FIG. 3D is a schematic diagram of a fluorescence measurement unit for measuring the color and fluorescence intensity of a fluorescent dye contained in droplets or wells in one embodiment of the present invention.

In the example of the fluorescence measurement unit shown in FIG. 3A, the fluorescence intensity of droplets is measured using a micro flow path. Droplets 301 flow in a micro flow path 303 in the direction of an arrow. When droplets flow and reach the position corresponding to the droplet 302, they are irradiated with excitation light from a light source 304 while being heated with a heater (not shown in the figure). A fluorescent substance contained in the droplets is excited with the light source 304 to emit fluorescence, and the fluorescence is detected through a fluorescence filter 305 with a photomultiplier-meter 306. Detected fluorescence data is sent to a calculator (not shown in the figure), and a melting temperature between the fluorescent-labeled probe and DNA or a melting temperature of a double strand DNA is calculated with the calculator. A respective fluorescence detector composed of a light source 304, a fluorescence filter 305 and a photomultiplier-meter 306 may be provided for each color of fluorescent dyes. Alternatively, as shown in FIG. 3A, the florescence detector may be configured so as to excite with excitation light from a single light source and detect two types of fluorescence simultaneously through respective fluorescence filters.

Figures 3B, 3C, 3D:
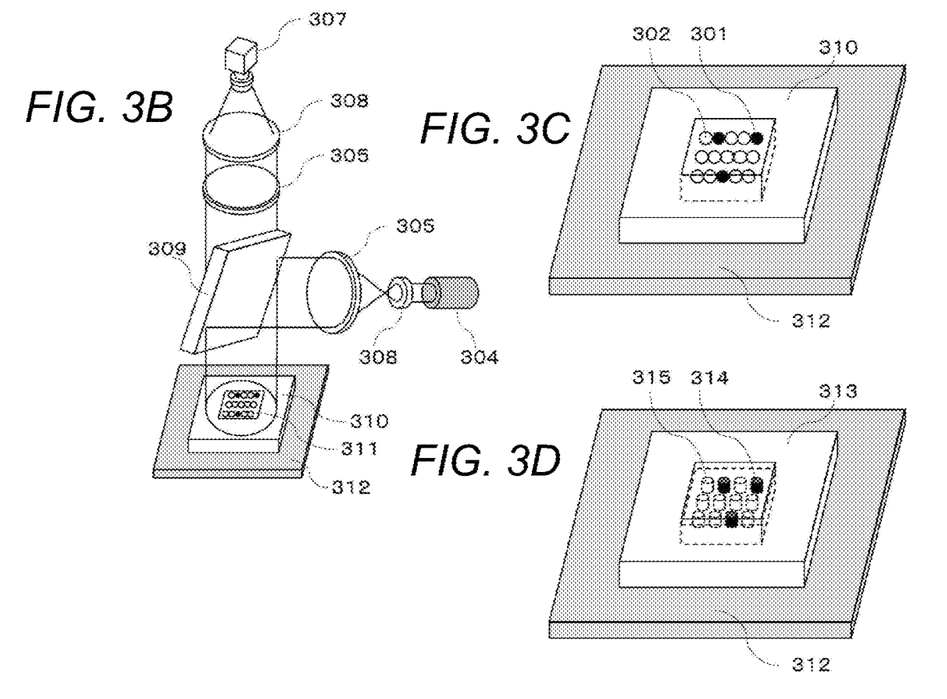

Furthermore, as shown in FIGS. 3B and 3C, droplets may be arranged planarly to measure the color and fluorescence intensity of a fluorescent dye in the droplets. Specifically, for example, droplets 311 are planarly arranged on a droplet detection cartridge 310, which is set on a temperature control stage 312 that serves as a heater. The temperature of the droplet detection cartridge is changed with the temperature control device 312, and the fluorescence intensities of the droplets are measured in association with the temperature change in the following manner. First, the droplets 311 planarly arranged on a droplet detection cartridge 310 are irradiated with an excitation light through a lens 308, a filter 305 and a dichroic mirror 309 from a light source 304. A fluorescent substance contained in the droplets is excited with the excitation light, and the emitted fluorescence is detected through the dichroic mirror 309, the filter 305 and the lens 308 with a CCD camera 307. Detected fluorescence data is send to a calculator (not shown in the figure), and melting temperatures of amplicons are calculated with the calculator. In FIG. 3A, the droplets are required to be treated one by one. In contrast, in the devices shown in FIGS. 3B and 3C, many droplets can be treated at one time. Therefore, the devices shown in FIGS. 3B and 3C are preferred. Furthermore, the devices shown in FIGS. 3B and 3C, the temperature control device 312 can also be used are preferred than the device shown in FIG. 3A in that they can be used for a DNA amplification reaction.

Alternatively, as shown in FIG. 3D, using wells that are arranged in an array-like form in place of the droplets, the color and fluorescence intensity of a fluorescent dye in each of the wells can be measured after a sample is added to the wells such that one or zero molecule of a target gene is contained in a single well and PCR is carried in the wells; and. Specifically, for example, a reaction solution containing a sample is added to the wells in a well-type detection cartridge 313, then PCR is carried out in the wells, and then the cartridge 313 is set on a temperature control stage 312 that serves as a heater. The temperature of the well-type detection cartridge is changed with the temperature control device 312, and the fluorescence intensity of the wells is measured in association with the temperature change in the following manner. First, the wells planarly arranged in a well-type detection cartridge 313 are irradiated with an excitation light through a lens 308, a filter 305 and a dichroic mirror 309 from a light source 304. A fluorescent substance contained in a reaction solution in the wells is excited with the excitation light, and the emitted fluorescence is detected through the dichroic mirror 309, the filter 305 and the lens 308 with a CCD camera 307. Detected fluorescence data is send to a calculator (not shown in the figure), and melting temperatures of amplicons are calculated with the calculator. In the case that the wells are used in the manner shown in FIG. 3D, a process from PCR to a melting curve analysis can be carried out in a well-type detection cartridge without the step of planarly arranging droplets on a droplet detection cartridge.

(3) Melting Curve Analysis Method

Figure 4A:
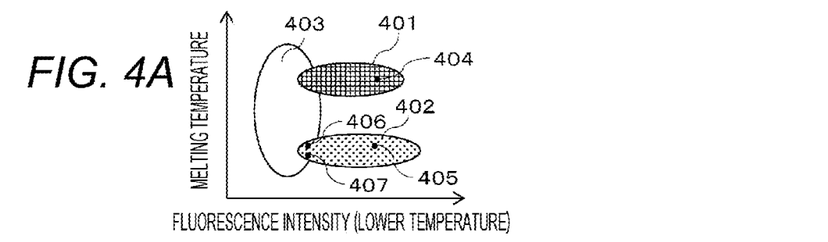
FIG. 4A to FIG. 4B illustrates (A) a diagram showing one example of a digital PCR measurement result obtained by a DNA detection method which is carried out using a melting temperature (Tm) of a PCR amplicon and (B) a diagram showing one example of a digital PCR measurement result obtained by a DNA detection method which is carried out using the ratio, in association with the temperature change of the fluorescence intensity of a PCR amplicon at a second temperature to that at a first temperature, the second temperature being lower than the first temperature, in one embodiment of the present invention.
Figure 4B:
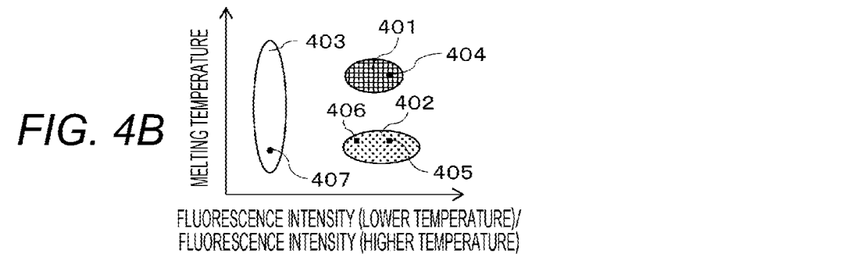

FIG. 4A is a schematic diagram showing one example of the measurement result obtained by the DNA detection method which is carried out using a melting temperature (Tm) of a PCR amplicon as mentioned with respect to FIG. 2 and in which detected fluorescence intensities may be overlapped with each other and the presence or absence of a target gene in a sample solution may not be determined. In contrast, FIG. 4B is a schematic diagram showing one example of the digital PCR measurement result obtained by the DNA detection method that is carried out using the ratio of the fluorescence intensity of a PCR amplicon at a second temperature that is lower than a first temperature in association with the temperature change to that at the first temperature as mentioned with respect to FIG. 1, in which the presence or absence of a target gene in a sample solution can be determined with higher accuracy. FIG. 5A to FIG. 5H and FIG. 6A to FIG. 6H are schematic diagrams showing examples of the result of the melting curve analysis of DNA that may have been amplified in each of sample solutions in which the presence or absence of a target gene to be detected have not been able to be determined in FIG. 4A to FIG. 4B.

As shown in FIG. 4A, when the genotype determination of a target gene to be detected in sample solutions is carried out based on a melting temperature and fluorescence intensity at a lower temperature, in the case that a measurement result is plotted at a position corresponding to a sample solution a404 or a sample solution b405, it is found, from the values of the melting temperatures, that the solution a404 contains the wild-type gene of the target gene and the sample solution b405 contains a mutant gene of the target gene. However, in the case that fluorescence intensity is observed at the position corresponding to a sample solution c406 or a sample solution d407, it is impossible to be determined, from the measurement results, whether or not these sample solutions contain the target gene.

Then, when the melting temperature of DNA molecules which have been amplified in a sample solution is measured using a DNA intercalator, the ratio of the fluorescence intensity at a lower temperature to the fluorescence intensity at a higher temperature is also calculated. As a result, the presence or absence of the target gene, which cannot be determined in FIG. 4A, can be determined. In a specific method, first, a DNA intercalator 502 is added to a PCR reaction solution to prepare a sample solution, which is subjected to a nucleic acid amplification reaction such as PCR. As a result, the DNA intercalator 502 is bound to double-strand DNA 501 that has been amplified in the sample solution and intense fluorescence is emitted at a temperature around the room temperature. Thereafter, the double strand DNA 501 in the sample solution is dissociated to produce single-stranded DNA with the increase of the temperature of the sample solution. The DNA intercalator 502 is not bound to the single-stranded DNA 501 anymore and, as a result, the fluorescence intensity decreases. Examples of the result obtained by plotting the change in fluorescence intensity versus the change in temperature in a graph are shown in FIG. 5A to FIG. 5H. In this regard, the change in fluorescence intensity with the temperature change may be measured by increasing the temperature of the sample solution independently of a nucleic acid amplification reaction (e.g., after the completion of a nucleic acid amplification reaction).

Figure 5A:
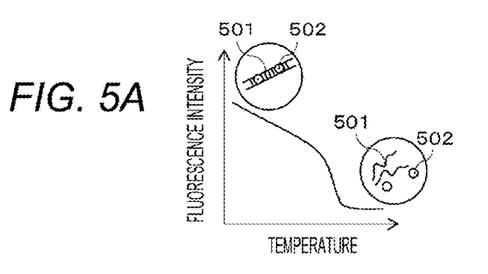
FIG. 5A to FIG. 5H illustrates schematic diagrams showing a method of measuring a melting temperature of DNA using a DNA intercalator in a DNA detection method according to one embodiment of the present invention, which is carried out using the ratio, in association with the temperature change, of the fluorescence intensity at a second temperature to that at a first temperature, the second temperature being lower than the first temperature.
Figure 5B:
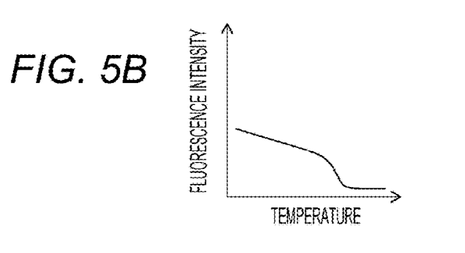
Figure 5C:
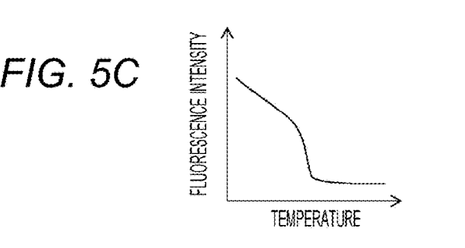
Figure 5D:
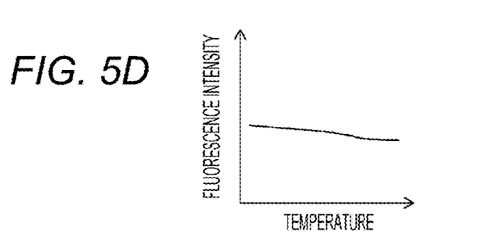
Figure 5E:
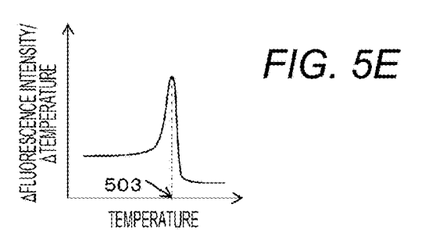
Figure 5F:
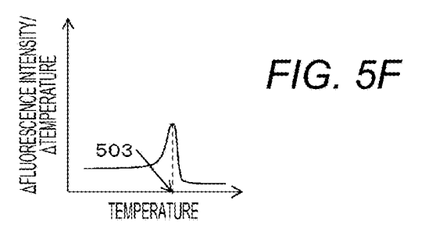
Figure 5G:
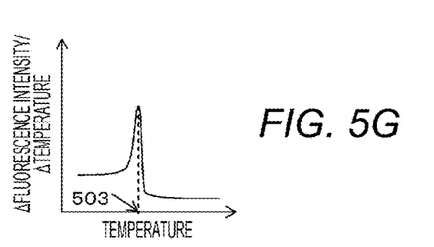
Figure 5H:
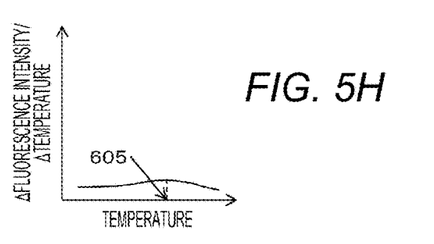

In FIG. 5A to FIG. 5H, the measurement result for a sample solution a404 is shown in FIG. 5C, the measurement result for a sample solution b405 is shown in FIG. 5A, the measurement result for a sample solution c406 is shown in FIG. 5B, and the measurement result for a sample solution d407 is shown in FIG. 5D. Furthermore, when the changes in fluorescence intensities shown in FIGS. 5A to 5D are differentiated with the temperature change, the results shown in FIGS. 5E to 5H are obtained. As a result, a temperature that corresponds to an inflection point of the change in fluorescence intensity can be calculated and obtained as the melting temperature of a DNA double strand. In FIG. 4A, with respect to the sample solution c406 and the sample solution d407, it cannot be determined, from the measurement results, whether or not the sample solutions contain the target gene. The change in fluorescence intensity in association with the temperature change shown in FIG. 5B is large, but is small in FIG. 5D. Accordingly, the ratio of fluorescence intensity at a lower temperature to that at a higher temperature is defined by the x-axis and the melting temperature is defined by the y-axis as shown in FIG. 4B, and it is thus determined that the sample solution c406 contains the wild-type of the target gene and the sample solution d407 is an empty solution that does not contain the target gene.

The melting temperature of a target gene can be controlled depending on the sequence and length of the PCR amplicon by changing the designs of primers.

Here, any DNA intercalator can be used, as long as the fluorescence intensity increases upon binding to double strand DNA and therefore can be used for detection of the double strand DNA. Specifically, the following DNA intercalators are applicable: SYBR (registered trademark) Green I and SYBR Gold, PicoGreen (registered trademark), SYTO (registered trademark) Blue, SYTO Green, SYTO Orange, SYTO Red, POPO (registered trademark)-1, BOBO (registered trademark)-1, YOYO (registered trademark)-1, TOTO (registered trademark)-1, JOJO (registered trademark)-1, POPO-3, LOLO (registered trademark)-1, BOBO-3, YOYO-3, TOTO-3, PO-Pro (registered trademark)-1, YO-Pro (registered trademark)-1, TO-Pro (registered trademark)-1, JO-Pro (registered trademark)-1, PO-Pro-3, YO-Pro-3, TO-Pro-3, TO-Pro-5 and ethidium bromide. In the case that the DNA intercalator is heat-resistant, the DNA intercalator can be added to the droplets prior to the PCR reaction.

As shown in FIG. 6A to FIG. 6H, in the present method, fluorescent-labeled probes may be used in place of the DNA intercalator. Each of the fluorescent-labeled probes is designed to have such a structure as follows: it has a fluorescent dye and a quencher for the fluorescent dye at respective terminals or in the respective vicinities thereof; sequences in the vicinities of the both terminals are complementary to each other and the probe forms a stem-loop structure like a molecular beacon; and the sequence for a loop moiety is complementary to a target gene to be detected and can hybridize with the target gene. When a fluorescent-labeled probe 602 is present singly in a free form, the stem-loop structure is formed so that a fluorescent dye 603 and a quencher 604 are in close proximity to each other; thus, fluorescence is not emitted. When the fluorescent-labeled probe 602 is added to a sample solution in which the PCR reaction has been completed, at a temperature around room temperature, the loop moiety in the fluorescent-labeled probe 602 is annealed to DNA 601 amplified in the sample solution and a fluorescent dye 603 and a quencher 604 are separated from each other; thus, the fluorescent-labeled probe 602 emits intense fluorescence. When the sample solution is heated thereafter, the DNA 601 and the fluorescent-labeled probe 602 are dissociated from each other to form the stem-loop structure in the fluorescent-labeled probe 602; thus, the intensity of fluorescence from the fluorescent-labeled probe 602 is decreased. When the sample solution is further heated, the stem-loop structure in the fluorescent-labeled probe 602 is also dissociated; thus, the intensity of fluorescence increases again. In this case, examples of the result obtained by plotting the change in fluorescence intensity with the temperature change on a graph are shown in FIG. 6A to FIG. 6H. The fluorescent-labeled probe may be the same as the fluorescent-labeled probe for the PCR. Alternatively, a probe that is different from the fluorescent-labeled probe for the PCR may be prepared and used. The change in fluorescence intensity with the temperature change may be measured during a nucleic acid amplification reaction, or by increasing the temperature of the sample solution independently of a nucleic acid amplification reaction (e.g., after the completion of a nucleic acid amplification reaction).

Figure 6A:
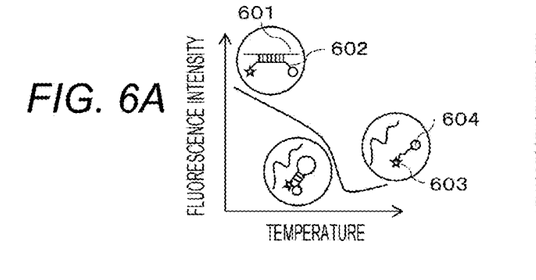
FIG. 6A to FIG. 6H illustrates schematic diagrams showing a method of measuring a melting temperature of DNA using a fluorescent-labeled probe in a DNA detection method according to one embodiment of the present invention, which is carried out using the ratio, in association with the temperature change, of the fluorescence intensity at a second temperature to that at a first temperature, the second temperature being lower than the first temperature.
Figure 6B:
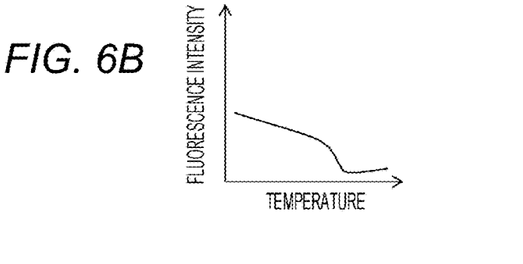
Figure 6C:
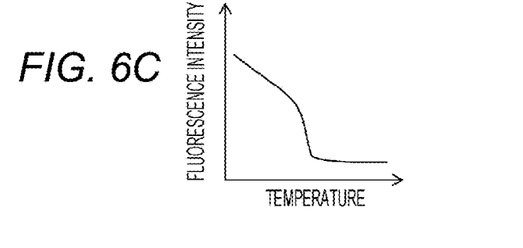
Figure 6D:
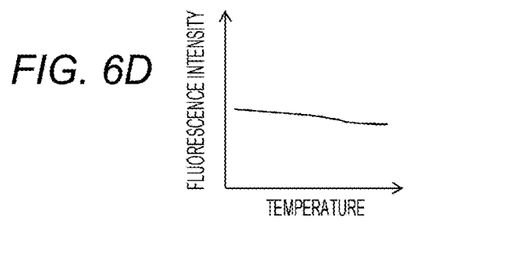
Figure 6E:
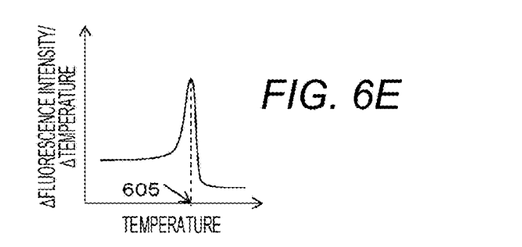
Figure 6F:
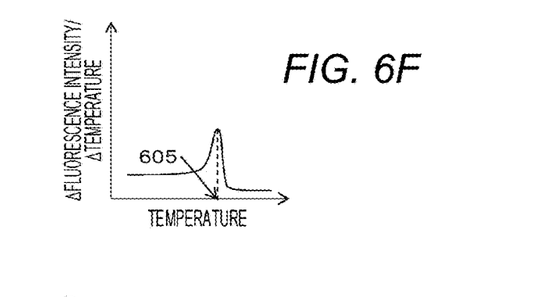
Figure 6G:
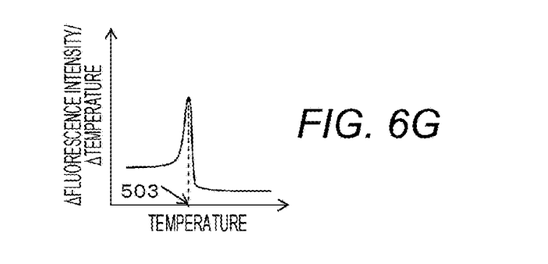
Figure 6H:
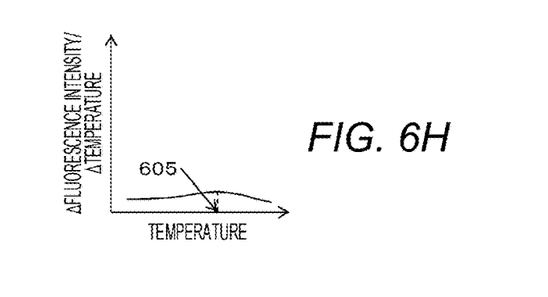

In FIG. 6A to FIG. 6H, the measurement result for a sample solution a404 is shown in FIG. 6C, the measurement result for a sample solution b405 is shown in FIG. 6A, the measurement result for a sample solution c406 is shown in FIG. 6B, and the measurement result for a sample solution d407 is shown in FIG. 6D. Furthermore, when the changes in fluorescence intensities shown in FIGS. 6A to 6D are differentiated with the temperature change, the results shown in FIGS. 6E to 6H are obtained and a temperature that corresponds to an inflection point of the change in fluorescence intensity can be determined, and is defined as a melting temperature between a fluorescent-labeled probe for detecting the target gene and DNA. In FIG. 4A, it cannot be determined, from the measurement results, if the sample solution c406 and the sample solution d407 contain the target gene. The change in fluorescence intensity with the temperature change is large in FIG. 6B, but is small in FIG. 6D. Then, the ratios of fluorescence intensity at a lower temperature to that at a higher temperature are plotted on the x-axis and the melting temperatures are plotted on the y-axis as shown in FIG. 4B and it is then determined that the sample solution c406 contains the wild-type of the target gene and the sample solution d407 is an empty solution which does not contain the target gene.

The melting temperature of a fluorescent-labeled probe for detecting a target gene to be detected can be controlled by adjusting the sequence or length of the probe. The melting temperature can also be controlled by utilizing artificial DNA such as Peptide Nucleic Acid (PNA) and Locked Nucleic Acid (LNA).

The combination of the fluorescent dye 603 and the quencher 604 in the fluorescent-labeled probe 602 is not particularly limited, as long as it has been used conventionally in real-time PCR. FAM, VIC, ROX, Cy3 and Cy5 are exemplified as the fluorescent dye 603 and TAMRA, BHQ1, BHQ2 and BHQ3 are exemplified as the quencher 604.

The sequences recognized by the fluorescent-labeled probes 602 may be located on the target gene or on different genes which include the target gene and a gene comprising a sequence in which only a single nucleotide is different from the target gene, such as a wild-type and mutant of the same gene. For example, in the case that the genetic test on lung cancer is to be carried out, the presence or absence of the ALK fusion gene and the presence or absence of an mutation of the EGFR gene are determined in order to predict the efficacy of a molecular target drug. In this case, the fluorescent-labeled probes 602 may have sequences which can recognize both of the ALK fusion gene and EGFR gene, or may have sequences which can recognize both of a L858R mutant of EGFR and the wild-type of EGFR.

(4) Other Configuration of DNA Detection Device

The DNA detection device according to one embodiment of the present invention may include a droplet generation unit for adding a DNA solution containing a target DNA to be detected to an oil to generate droplets and/or an amplification unit for amplifying the DNA in the droplets.

Figure 7A:
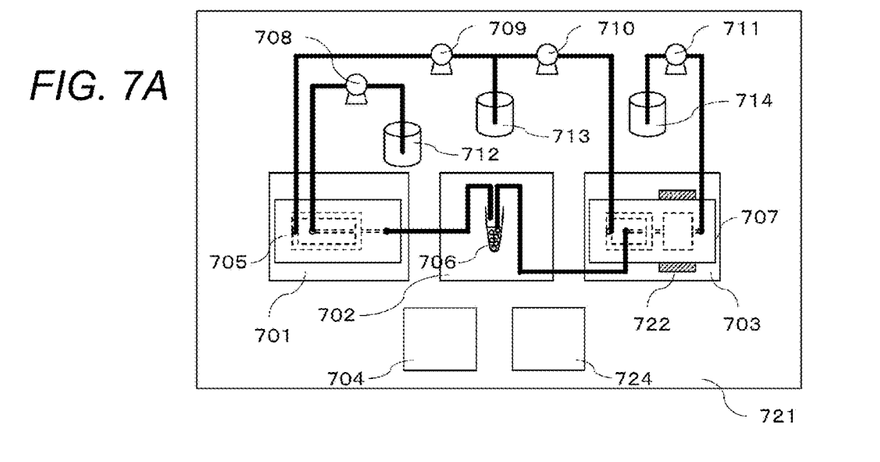
FIG. 7A to FIG. 7C illustrates schematic diagrams showing a device for carrying out a DNA detection method according to one embodiment of the present invention and a cartridge used in the device.
Figure 7B:
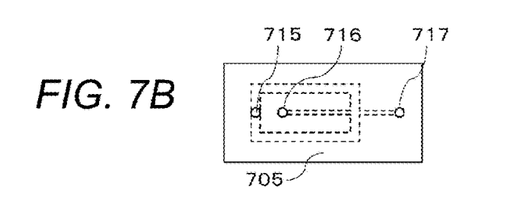
Figure 7C:
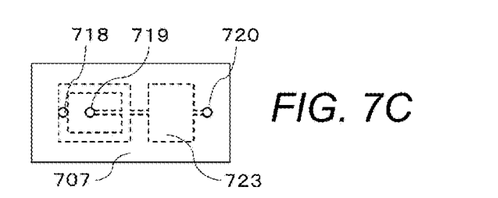

FIG. 7A to FIG. 7C illustrates diagrams showing one example of the device for carrying out the method of the present invention and one example of the cartridge used in the device. As shown in FIG. 7A, a digital PCR measurement device 721 is composed of a droplet generation unit 701, a thermal cycler 702 that serves as an amplification unit, a droplet detection unit 703, a monitor 704 and a controller 724. In the droplet generation unit 701, a droplet generation cartridge 705 shown in FIG. 7B is set upon use. The droplet generation cartridge 705 is equipped with an oil supply port 715, a PCR reaction solution inlet port 716 and a droplet discharge port 717. In the droplet detection unit 703, a droplet detection cartridge 707 shown in FIG. 7C is set on a temperature control device 722 upon use. The droplet detection cartridge 707 is equipped with an oil supply port 718, a droplet inlet port 719, a liquid reservoir 723 and a waste discharge port 720. The oil supply port 715 in the droplet generation cartridge is fluidically connected to the digital PCR measurement device 721 and an oil 713 is supplied to the oil supply port 715 by means of a pump 709. The PCR reaction solution inlet port 716 in the droplet generation cartridge is fluidically connected to the digital PCR measurement device 721 and a gas such as a nitrogen gas and air or an oil 712 is supplied to the PCR reaction solution inlet port 716 by means of a pump 708. The droplet discharge port 717 in the droplet generation cartridge is fluidically connected to the digital PCR measurement device 721, and is connected to a microtube 706 set on the thermal cycler 702. The oil supply port 718 in the droplet detection cartridge 707 is fluidically connected to the digital PCR measurement device 721, and the oil 713 is supplied by means of a pump 710. The droplet inlet port 719 in the droplet detection cartridge 707 is fluidically connected to the digital PCR measurement device 721, and is connected to the microtube 706 set on the thermal cycler 702. The waste discharge port 720 in the droplet detection cartridge 707 is fluidically connected to the digital PCR measurement device 721, and waste in the droplet detection cartridge 707 is discharged to the waste reservoir 714 by means of a pump 711. The pump may be a perista pump, a syringe pump or a diaphragm pump. The monitor 704 is a display on which measurement results or messages are to be displayed, and is also be an input unit on which a user inputs an operation.

The DNA detection device according to another aspect of the present invention may include a chip preparation unit for applying a DNA solution containing a target DNA to be detected onto wells arranged in an array-like form on a chip and/or an amplification unit for amplifying DNA in the wells.

(5) Melting Temperature Measurement Method

Figure 8:
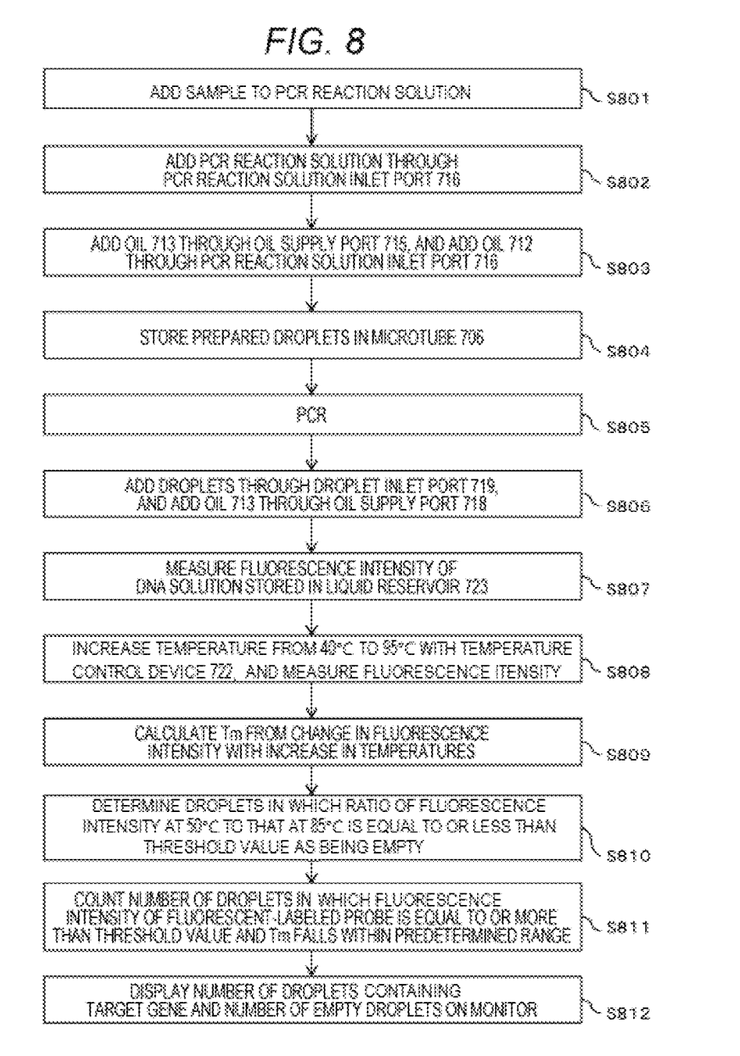
FIG. 8 is a flow chart showing one embodiment of the method for carrying out the measurement of a melting temperature using the device and the cartridge both shown in FIG. 7A to FIG. 7C.

Hereinbelow, one example of the method for measuring a melting temperature using the device and the cartridge shown in FIG. 7A to FIG. 7C and a DNA intercalator or a molecular beacon will be described with reference to the flow chart shown in FIG. 8. First, a sample solution derived from a DNA-containing biological sample is added to a PCR reaction solution containing a DNA polymerase, a primer, a DNA intercalator or a molecular beacon, deoxyribonucleotides and a buffer (S801). The PCR reaction solution is added to a PCR reaction solution inlet port 716 in a droplet generation cartridge 705 (S802). The droplet generation cartridge 705 is set in a droplet generation unit 701 in a digital PCR measurement device 721. An oil 713 is added through an oil supply port 715 and an oil 712 is added through the PCR reaction solution inlet port 716 (S803), whereby droplets are generated in a site at which the oil in the droplet generation cartridge 705 and the flow path of the PCR reaction solution intersect each other. The droplets thus generated are discharged through a droplet discharge port 717, then move to a microtube 706 that has been installed in a thermal cycler in advance, and are then stored in the tube (S804). When a certain number of droplets are obtained, a lid of the microtube 706 is closed, and PCR is carried out while controlling the temperature by the thermal cycler (S805). A cycle of a denaturation step, an extension step and an annealing step is repeated to amplify the DNA. The DNA intercalator intercalates into the amplified DNA and the molecular beacon hybridizes to the amplified DNA; thereby, the fluorescence intensity is increased. The reaction conditions including the temperature and time of each of the steps and the number of cycles can be adjusted easily by a person skilled in the art. After the PCR, the temperature is decreased to room temperature to cause the synthesized DNA to form a double strand. After the PCR, the droplets are added through a droplet inlet port 719 in a droplet detection cartridge that has been installed in the droplet detection unit 703 in advance and the oil 713 is added through an oil supply port 718 (S806). In the droplet detection unit 703, the fluorescence intensity of a fluorescent-labeled probe in the droplets stored in a liquid reservoir 723 in the droplet detection cartridge is measured (S807). The temperature of the liquid reservoir 723 in the droplet detection cartridge is increased from 50° C. to 85° C. with a temperature control device 722, and the intensity of fluorescence from the DNA intercalator or the molecular beacon is measured (S808). The detected fluorescence data is sent to a calculator (not shown in the figure), the change in fluorescence intensity with the increase in temperatures is differentiated with the temperature change with the calculator, and an inflection point of the change in fluorescence intensity is determined as a melting temperature (S809). A droplet in which the ratio of the fluorescence intensity at 40° C. to the fluorescence intensity at 95° C. is equal to or less than a threshold value is determined as being empty (S810). The number of droplets in which the fluorescence intensity of the fluorescent-labeled probe is equal to or more than a threshold value and the melting temperature falls within a predetermined range is counted (S811). The number of droplets containing the target gene and the number of empty droplets are displayed o a monitor (S812). The predetermined threshold value of fluorescence intensity and the predetermined range of the melting temperature can be determined in advance by a practitioner by carrying out pilot experiments and the like.

The sample solution to be used is not particularly limited, and any sample containing a target DNA to be detected may be used. Examples of the sample solution include: a biological sample, such as excrement, a tissue, a cell and a body fluid of an animal or a plant; and a sample containing fungi or bacteria, such as a soil sample. Examples of the body fluid include blood, saliva and spinal fluid, and blood contains cell free DNA (cfDNA) and circular tumor DNA (ctDNA). Examples of the tissue include a disease-affected site which is obtained by a surgical operation or a biopsy (e.g., a cancer tissue in breast, liver or the like). The tissue may be a fixed tissue, such as a formalin-fixed paraffin-embedded (FFPE) tissue. Examples of the cell include: a cell in an affected site or a site in the vicinity of the affected site, which is collected by a biopsy; and a tumor cell which circulates in blood. The pretreatment of the sample is not particularly limited. The sample which has been collected from a living body or an environment may be used only after homogenized in a suspension or dissolved in a dissolution solution. However, it is preferred to use nucleic acid extracted or purified from them.

The oil is preferably a chemically inert substance that is insoluble or poorly soluble in a PCR reaction solution constituting the droplets and is stable against the temperature change in a higher temperature range such as for in PCR. As the oil, a fluorine-based oil, a silicone-based oil, a hydrocarbon-based oil and the like can be used. Examples of the fluorine-based oil include perfluorocarbon and hydrofluoroether. The fluorine-based oil preferably has a longer carbon chain, because of low volatility. The fluorine-based oil has a specific gravity of more than 1.7, which is larger than the specific gravity (i.e., 1) of water that is a solvent for a PCR reaction solution. Therefore, the generated droplets can float on the oil. Examples of the silicone-based oil include polyphenylmethylsiloxane and trimethylsiloxysilicate. Unlike the fluorine-based oil, the silicone-based oil has a specific gravity of about 0.98 which is close to the specific gravity of water that is a solvent for a PCR reaction solution. Therefore, the generated droplets can be uniformly distributed in the oil. Examples of the hydrocarbon-based oil include mineral oil, liquid paraffin and hexadecane. The hydrocarbon-based oil has a specific gravity of about 0.84, which is smaller than the specific gravity of water that is a solvent for a PCR reaction solution. Therefore, the generated droplets can sink in the oil.

A surfactant may be added to the oil upon the use of the oil. The type of the surfactant is not particularly limited, and Tween 20, Tween 80, Span80, Triton X-100 and the like are applicable.

(6) Display of Results

Figure 9:
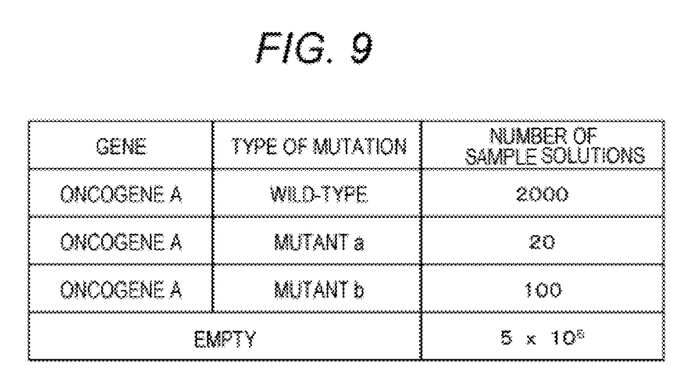
FIG. 9 illustrates one example of a measurement result displayed on a monitor.
Figure 10:
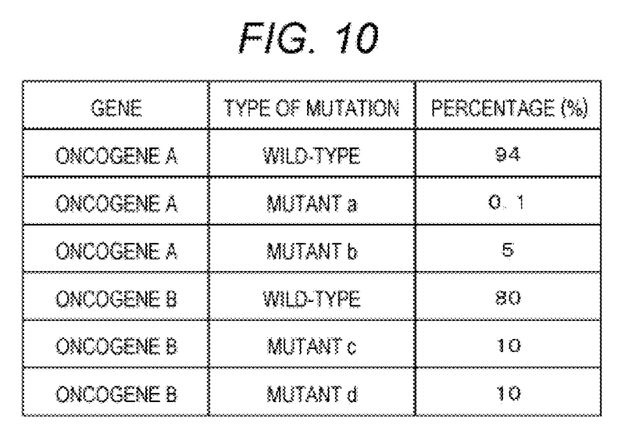
FIG. 10 illustrates one example of a measurement result displayed on a monitor.
Figure 11A:
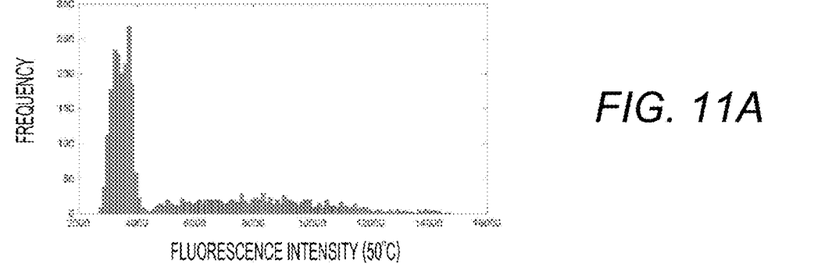
FIG. 11A to FIG. 11E illustrates graphs showing the results of determining, using a fluorescent-labeled probe, whether or not a target gene is present in wells in one example of the present invention.
Figure 11B:
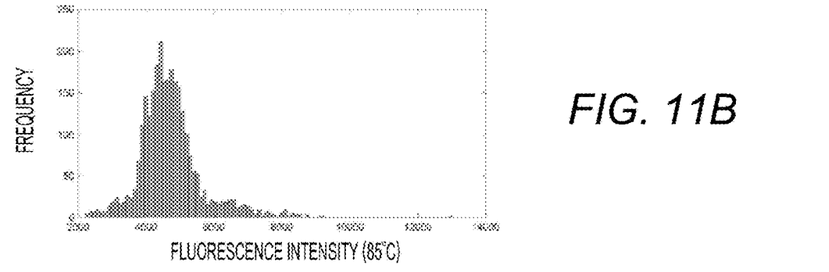
Figure 11C:
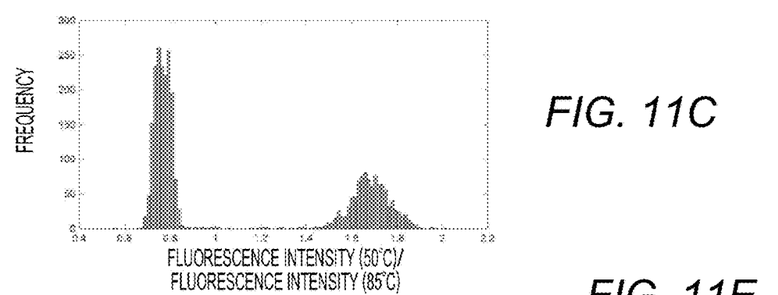
Figure 11D:
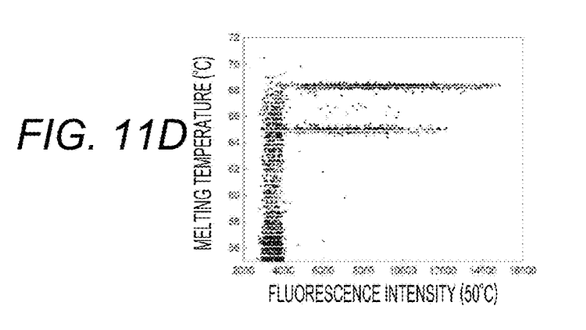
Figure 11E:
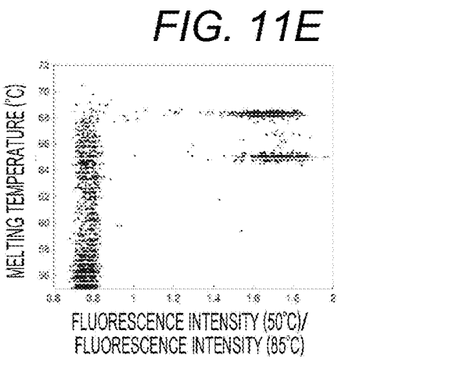

FIGS. 9 and 10 show examples of the image of the measurement result to be displayed on a monitor. The number of sample solutions which is counted for every oncogene type and every mutation type may be displayed, as shown in FIG. 9. Alternatively, the percentage of sample solutions which is counted for every oncogene type and every mutation type may be displayed, as shown in FIG. 10. In addition to the number and percentage of sample solutions as shown in FIGS. 9 and 10, the result to be displayed on the monitor may further include a graph produced by plotting measurement values for sample solutions on two axes, in which the ratios of fluorescence intensity at a lower temperature to that at a higher temperature are indicated on one axis and the melting temperatures are indicated on the other axis as shown in FIG. 1. The result to be displayed on the monitor may also include a histogram produced by plotting the number of sample solutions to the fluorescence intensity or melting temperature of a fluorescent-labeled probe. It is possible for a user to change the threshold value for the fluorescence intensity or fluorescence intensity ratio of a fluorescent-labeled probe and/or the range of the melting temperature referring to the graph or histogram and then count again the number of sample solutions which show fluorescence intensity equal to or less than the threshold value and a melting temperature falling within the range.

As mentioned above, a sample solution is handled as droplets or solutions partitioned in wells. Therefore, the number of droplets or wells may be used in place of the number of sample solutions.

(6) Program

One embodiment of the present invention is a program for allowing a DNA detection device to execute a DNA detection method. The DNA detection device to be used is the device described in detail in section (2), and the DNA detection method to be executed is the method described in detail in section (1).

A recording medium for storing the program therein is also one embodiment of the present invention.

EXAMPLES

In this example, the results obtained by measuring the melting temperature of DNA in wells using a fluorescent-labeled probe are shown.

Genomic DNAs for wild-type and G12D mutant of KRAS gene were prepared (final concentration: 67 molecules/μL), and then a forward primer (final concentration: 0.25 µM), a reverse primer (final concentration: 0.5 µM), a fluorescent-labeled probe corresponding to the wild-type (final concentration: 0.5 nM), a fluorescent-labeled probe corresponding to the G12D mutant (final concentration: 0.5 µM) and a 1× Master Mix (containing a DNA polymerase and dNTPs) which were necessary for PCR were added to the genomic DNAs to prepare PCR reaction solutions. In order to amplify a complementary DNA strand of the fluorescent-labeled probe excessively, the primer pair was added such that the concentrations of the primers of the primer pair are not the same. The sequences for the primers and the probes are shown below. Each of the fluorescent-labeled probes included special molecules capable of forming a complementary strand at both terminals. In each of the fluorescent-labeled probes, FAM was conjugated to the 5'-terminal as a fluorescent dye and BHQ-1 was conjugated to the 3'-terminal as a quencher.

```
Forward primer:
                                      (SEQ ID NO: 1)
5'-AGGCCTGCTGAAAATGACTGAATAT-3'

Reverse primer:
                                      (SEQ ID NO: 2)
5'-GCTGTATCGTCAAGGCACTCTT-3'

Fluorescent-labeled probe corresponding to
wild-type:
                                      (SEQ ID NO: 3)
5'-TTGGAGCTGGTGGCGT-3'

Fluorescent-labeled probe corresponding to mutant:
                                      (SEQ ID NO: 4)
5'-TTGGAGCTGATGGCGT-3'
```

Subsequently, 15 µL of the PCR reaction solution was placed in each well such that a single molecule or no molecule of DNA for the wild-type or the G12D mutant of KRAS gene was contained in a single well, and the DNA was amplified by PCR. The PCR reaction was carried out as follows: a treatment at 95° C. for 10 minutes was carried out, then 45 cycles of (95° C., 15 seconds→60° C., 75 seconds) were carried out, and finally a treatment at 98° C. for 2 minutes was carried out. After the reaction, the change in fluorescence intensity in each of the wells was observed while heating, on a temperature control stage, a chip having the wells arranged thereon, and the measurement and analysis of melt curves were carried out.

FIG. 12A shows a histogram of fluorescence intensities at 50° C. when only the wild-type KRAS gene was added to the PCR reaction solution. At 50° C., in wells which contained the wild-type KRAS gene, the amplified DNA molecule and the fluorescent-labeled probe were hybridized with each other to emit fluorescence. As a result, two peaks each corresponding to the empty wells or the wells containing the wild-type KRAS gene were observed. However, a peak corresponding to the wells containing the wild-type KRAS gene was small in height and was broad; and therefore it was difficult to distinguish the wells from the empty wells.

FIG. 12B shows a histogram of fluorescence intensities at 85° C. when only the wild-type KRAS gene was added to the PCR reaction solution. At 85° C., the amplified DNA molecule and the fluorescent-labeled probe which had been hybridized with each other were dissociated, and the fluorescence intensity of wells containing the wild-type KRAS gene was decreased and became similar to the fluorescence intensity of empty wells. Therefore, peaks each corresponding to the two types of the wells overlapped each other to form a single peak. Namely, it could be understood that the change in fluorescence intensity in association with the temperature change was small in the empty wells, while the change in fluorescence intensity in association with the temperature change was large in the wells containing the wild-type KRAS gene.

Then, as shown in FIG. 12C, a histogram was produced using the ratio of fluorescence intensity at 50° C. to fluorescence intensity at 85° C. As a result, a peak corresponding to the empty wells and a peak corresponding to the wells containing the wild-type KRAS gene were distinguished clearly from each other.

Next, the wild-type and G12D mutant of KRAS gene were mixed together, and the genotypes was determined. The reaction conditions were the same as those mentioned above. FIG. 12C is a graph produced by plotting the fluorescence intensities of the wells at 50° C. on the x-axis and the melting temperatures on the y-axis. A cluster corresponding to the empty wells was observed at a fluorescence intensity of around 4000, and a cluster corresponding to the wells containing the wild-type or G12D mutant of KRAS gene was observed at a fluorescence intensity from around 4000 to 14000. The G12D mutant of KRAS gene had the sequence in which one nucleotide in the sequence for the wild-type was mutated from guanine to adenine, and had a lower melting temperature than that of the wild-type. Accordingly, the cluster appearing at a melting temperature of about 68° C. was that corresponding the wild-type, and the cluster appearing at a melting temperature of around 65° C. was that corresponding to the mutant. However, both of the wild-type and the G12D mutant showed large fluctuations in fluorescence intensity. Therefore, it was difficult to identify empty wells in a part of the region.

FIG. 12D is a graph produced by plotting the ratios of the fluorescence intensity at 50° C. to the fluorescence intensity at 85° C. on the x-axis and the melting temperatures on the y-axis. As the result of plotting the ratios of the fluorescence intensity at 50° C. to the fluorescence intensity at 85° C. on the x-axis, the wells containing KRAS gene showed smaller fluctuations along the x-axis direction and it was possible to clearly distinguish a cluster corresponding to the empty wells, a cluster corresponding to the wells containing the wild-type and a cluster corresponding to the wells containing the G12D mutant from one another.

As mentioned above, using the ratio of fluorescence intensity at a lower temperature to that at a higher temperature, it becomes possible to distinguish empty droplets that do not contain a target gene by using a measurement device, which leads to the improvement in measurement reproducibility and measurement accuracy.

INDUSTRIAL APPLICABILITY

According to the present invention, it becomes possible to provide a novel digital PCR analysis method which enables the highly accurate identification of empty droplets that do not contain a target gene in digital PCR using a melting curve analysis and which has high measurement reproducibility and high measurement accuracy.

REFERENCE SIGNS LIST

101 droplet containing the wild-type gene
102 droplet containing the mutant gene
103 empty droplet
201 droplet containing the wild-type gene 202 droplet containing the mutant gene
203 empty droplet
301 droplet containing the target gene
302 droplet not containing the target gene
303 micro flow path
304 light source
305 filter
306 photomultiplier-meter
307 CCD
308 lens
309 dichroic mirror
310 droplet detection cartridge
311 droplet
312 temperature control device
313 well-type detection cartridge
314 well containing the target gene
315 well not containing the target gene
401 droplet containing the wild-type gene
402 droplet containing the mutant gene
403 empty droplet
404 droplet a
405 droplet b
406 droplet c
407 droplet d
501 DNA
502 DNA intercalator
503 melting temperature
601 DNA
602 fluorescent-labeled probe
603 fluorescent dye
604 quencher
605 melting temperature
701 droplet generation unit
702 thermal cycler
703 droplet detection unit
704 monitor
705 droplet generation cartridge
706 microtube
707 droplet detection cartridge
708~711 pump
712 oil
713 oil
714 waste reservoir
715 oil supply port
716 PCR reaction solution inlet port
717 droplet discharge port
718 oil supply port
719 droplet inlet port
720 waste discharge port
721 digital PCR measurement device
722 temperature control device
723 liquid reservoir
724 controller

---

The invention claimed is:

1. A DNA detection method comprising the steps of:
partitioning a DNA solution comprising a fluorescent-labeled probe or a DNA intercalator and a target DNA to be detected into a plurality of compartments;
carrying out a nucleic acid amplification reaction in the compartments;
for each of the compartments, measuring a fluorescence intensity in association with a temperature change;
for each of the compartments, calculating, in association with the temperature change, a melting temperature of a DNA double strand based on a change in the fluorescence intensity;
calculating, in association with the temperature change, for each of the compartments a ratio of a fluorescence intensity at a second temperature to a fluorescence intensity at a first temperature, the second temperature being lower than the first temperature.

2. The DNA detection method according to claim 1, further comprising the step of specifying a compartment for which the calculated ratio of the fluorescence intensity is equal to or lower than a predetermined threshold as a compartment that does not contain the target DNA to be detected.

3. The DNA detection method according to claim 1, further comprising the step of specifying a compartment for which the calculated ratio of the fluorescence intensity falls within a predetermined range as a compartment that contains the target DNA to be detected.

4. The DNA detection method according to claim 1, wherein the DNA solution comprises a fluorescent-labeled probe and the melting temperature is a melting temperature of a double strand formed between the fluorescent-labeled probe and the target DNA to be detected.

5. The DNA detection method according to claim 4, wherein the fluorescent-labeled probe has a fluorescent dye and a quencher for the fluorescent dye.

6. The DNA detection method according to claim 1, wherein the DNA solution comprises a DNA intercalator and the melting temperature is a melting temperature of a double strand of the target DNA to be detected.

7. The DNA detection method according to claim 1, wherein the plurality of compartments are arranged planarly.

8. The DNA detection method according to claim 1, wherein the DNA solution is partitioned into the plurality of compartments in a form of droplets or by using wells.

9. A DNA detection device for detecting a target DNA to be detected in a DNA solution, comprising:
a heater for heating the DNA solution;
a fluorescence measurement unit for measuring an intensity of fluorescence emitted from the DNA solution; and
a calculator configured to calculate a melting temperature of a DNA double strand based on the change in the fluorescence intensity in association with a temperature change of the DNA solution, and then calculate a ratio of the fluorescence intensity at a second temperature to the fluorescence intensity at a first temperature, the second temperature being lower than the first temperature.

10. The DNA detection device according to claim 9, further comprising an amplification unit for amplifying the target DNA to be detected.

11. The DNA detection device according to claim 9, further comprising a monitor for displaying a detection result.

12. A non-transitory computer-readable storage medium containing instructions which when executed by a processor for allow a DNA detection device to execute a DNA detection method according to claim 1.

13. The non-transitory computer-readable storage medium according to claim 12, wherein the detection device is a DNA detection device for detecting a target DNA to be detected in a DNA solution, comprising:
a heater for heating the DNA solution;
a fluorescence measurement unit for measuring an intensity of fluorescence emitted from the DNA solution; and
a calculator for calculating a melting temperature of a DNA double strand based on the change in the fluorescence intensity in association with a temperature change of the DNA solution, and then calculating a ratio of the fluorescence intensity at a second temperature to the fluorescence intensity at a first temperature, the second temperature being lower than the first temperature.

14. The DNA detection method of claim 1, further comprising plotting a graph of the ratio for each of the compartments on a graph.

15. The DNA detection method of claim 14 further comprising selecting compartments based on the graph.

* * * * *

```
                     SEQUENCE LISTING

<160> NUMBER OF SEQ ID NOS: 4

<210> SEQ ID NO 1
<211> LENGTH: 25
<212> TYPE: DNA
<213> ORGANISM: Homo sapiens

<400> SEQUENCE: 1
aggcctgctg aaaatgactg aatat                                          25

<210> SEQ ID NO 2
<211> LENGTH: 22
<212> TYPE: DNA
<213> ORGANISM: Homo sapiens

<400> SEQUENCE: 2
gctgtatcgt caaggcactc tt                                             22

<210> SEQ ID NO 3
<211> LENGTH: 16
<212> TYPE: DNA
<213> ORGANISM: Homo sapiens

<400> SEQUENCE: 3
ttggagctgg tggcgt                                                    16

<210> SEQ ID NO 4
<211> LENGTH: 16
<212> TYPE: DNA
<213> ORGANISM: Homo sapiens

<400> SEQUENCE: 4
ttggagctga tggcgt                                                    16
```